United States Patent [19]

Margolin

[11] Patent Number: 5,019,048
[45] Date of Patent: May 28, 1991

[54] UNIT DOSE SYRINGE WITH ROTATABLE NEEDLE

[76] Inventor: George D. Margolin, 308 Vista Baya, Costa Mesa, Calif. 92627

[21] Appl. No.: 463,235

[22] Filed: Jan. 10, 1990

[51] Int. Cl.⁵ ............................................. A61M 5/32
[52] U.S. Cl. ................................. 604/153; 604/192; 604/204; 604/240
[58] Field of Search ............. 604/153, 187, 191, 192, 604/197, 200, 201, 204, 205, 206, 212, 240

[56] References Cited

U.S. PATENT DOCUMENTS

| | | | |
|---|---|---|---|
| 609,982 | 8/1898 | Winchester | 604/240 |
| 2,618,263 | 11/1952 | Lakso et al. | 604/204 X |
| 2,618,263 | 11/1952 | Lakso et al. | 128/216 |
| 2,642,064 | 6/1953 | Lawshe | 604/192 |
| 2,643,795 | 6/1953 | Teal | 222/93 |
| 2,679,951 | 6/1954 | Yantzer | 222/101 |
| 2,801,028 | 7/1957 | Ward et al. | 222/101 |
| 2,848,141 | 8/1958 | Intagliata | 222/101 |
| 2,888,924 | 6/1959 | Dunmire | 604/204 X |
| 2,907,326 | 10/1959 | Gerarde | 128/216 |
| 2,911,972 | 11/1959 | Elinger | 128/216 |
| 3,244,173 | 4/1966 | Berg | 604/192 |
| 3,276,632 | 10/1966 | Stanzel | 604/204 X |
| 3,367,331 | 2/1968 | Brookfield | 604/201 X |
| 3,401,695 | 9/1968 | Rosenberg et al. | 604/192 |
| 3,411,503 | 11/1968 | Santomieri | 128/216 |
| 3,643,837 | 2/1972 | Green | 222/101 |
| 3,736,933 | 6/1973 | Szabo | 604/200 |
| 3,780,911 | 12/1973 | Paige | 222/101 |
| 4,020,836 | 5/1977 | Cunningham | 604/204 X |
| 4,258,863 | 3/1981 | Ness | 222/83 |
| 4,447,232 | 5/1984 | Sealfon et al. | 604/134 |
| 4,502,616 | 3/1985 | Meierhoefer | 222/215 |
| 4,548,601 | 10/1985 | Lary | 604/204 |

Primary Examiner—John D. Yasko
Assistant Examiner—Adam J. Cermak
Attorney, Agent, or Firm—Herbert M. Shapiro

[57] ABSTRACT

A safely disposable unit dose syringe is achieved by sealing the fluid to be administered into a plastic or otherwise inexpensive, deformable container such as a plastic baggie and attaching to the container a needle which can be moved from a protected compartment to an exposed position for administering the fluid. The needle is withdrawn to the protected position after use for safe disposal. After use the container cannot be refilled without the use of fairly elaborate and costly equipment. The syringes can be produced in the form of a bandoleer for administration by means of a gun-like device, the contents of each syringe being delivered in response to the squeezing of a trigger-like mechanism.

15 Claims, 3 Drawing Sheets

UNIT DOSE SYRINGE WITH ROTATABLE NEEDLE

FIELD OF THE INVENTION

This invention relates to a syringe for the delivery of fluids into the human body, and more particularly to a disposable syringe.

BACKGROUND OF THE INVENTION

Disposable syringes are today in widespread use. Such a syringe is sold with an inexpensive plastic sleeve which covers the needle of the syringe and is sufficiently inexpensive to be thrown away. Unfortunately, syringes of this type are reusable and have become a source of serious contamination and spread of diseases such as AIDS.

BRIEF DESCRIPTION OF EMBODIMENTS OF THIS INVENTION

The invention is directed at a unit dose syringe which is impossible to reuse once its contents are dispensed. Moreover, the needle of the syringe is integral with the container and can occupy an exposed or protected position with respect to the container. The exposed position is for administering the contents of the container. The protected position is for safe transport and, after the contents are used, for safe disposal. In one embodiment, hinged portions of the container are spread apart, not only to expose the needle, but also to provide finger grips for the container. The container itself is a plastic squeeze bag.

In another embodiment, the container is a squeeze bag almost flat and in the shape of a credit card. The needle is housed in a pocket at an edge of the "credit card" and is hinged to perforate the squeeze bag when moved into the position required for use. In a related embodiment, a credit card-shaped squeeze bag has a hinged needle at more than one edge for providing a multiple dose syringe which is easily carried safely in a shirt pocket, wallet or purse. The needles are safely positioned flat against an edge of the squeeze bag. In each case, the edge is formed to accept the needle into a concealed and protected position.

In still another embodiment, again including a credit card-shaped squeeze bag, the needle itself is bent to form a head and stem portion. The stem portion is mounted onto a disc. When the disc is turned in first direction, the head portion is moved into a position for fluid delivery and the stem position is moved to open a passageway to the fluid. The disc is moved in the opposite direction after used to withdraw the head portion to a protected position for safe disposal.

DETAILED DESCRIPTION OF THE ILLUSTRATIVE EMBODIMENTS

Figure 1:
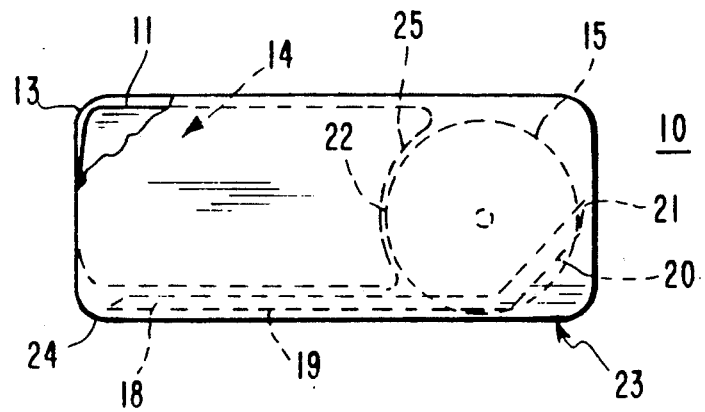
FIGS. 1 and 2 show schematic views of a credit card-shaped syringes with the needle in protected and exposed positions respectively.

FIG. 1 shows a syringe 10 in accordance with the principles of this invention. The syringe comprises a generally flat squeeze bag 11 including layers 13 and 14 which are sealed together at the edges to form a compartment for the fluid to be administered. The syringe also includes at least one disc-shaped element 15 moveable clockwise or counterclockwise in the plane of the compartment about an axis 17.

A needle 18 is shown in a protected position within the compartment. The needle is bent to form a head portion 19 and a stem portion 20. Stem portion 20 is secured to the disc-shaped element 15. When element 15 is rotated counterclockwise as viewed, head portion 19 is moved to the exposed position shown in FIG. 2 for administering the contents of the compartment. The stem portion, at this position, has a first end 21 which forms an opening at 22 in the compartment. The needle is withdrawn into the concealed position for safe disposal by rotating element 15 clockwise. FIG. 1 also shows a tear tab 23 which closes the recess 24 in compartment 11 which houses the needle in the protected position.

Compartment 11 is sealed from disc-shaped element 15 by a sealed edge 25 which closely fits about the edge of element 15. The opening 22 registers with the first end of stem portion 20 to avoid leaking when the needle is in the position shown in FIG. 1 yet allows the fluid to be injected when the needle is in the position shown in FIG. 2.

The first end of the stem portion is pointed as is the second end of the needle which is the end to be inserted into a patient.

Figure 3:
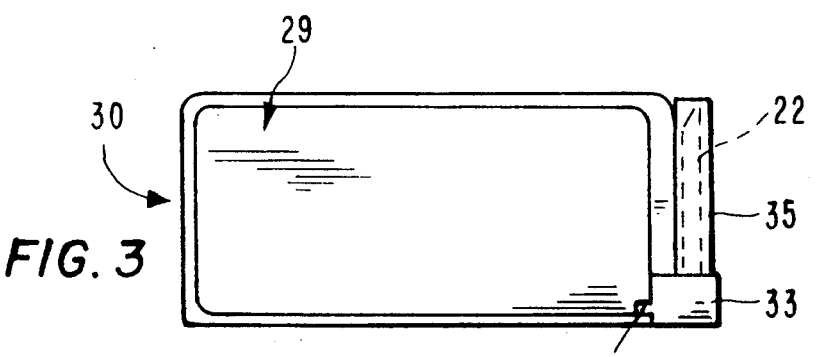
FIGS. 3 and 4, and 5 and 6 and 7 and 8 show schematic views of alternative credit card shaped syringes also with the needle in protected and exposed positions respectively.
Figure 4:
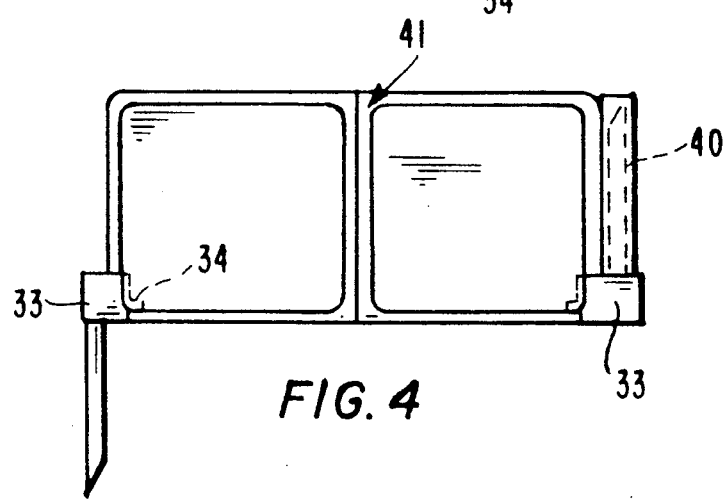

FIGS. 3 and 4 show an alternative syringe 30 with a compartment 29 formed by sealing two plastic layers together as discussed in connection with FIG. 1. The syringe also includes a needle 32 with a base hinged at 33. The base (or pivot) also includes a needle plunger 34. When the needle is rotated to a position shown in FIG. 4, the needle acts as a cam to advance plunger 34 into compartment 29.

In the exposed position for the needle as shown in FIG. 4, the compartment is perforated, the needle can be inserted and the contents administered by squeezing the compartment. In the protected position for the needle, as shown in FIG. 3, the needle resides in a recess 35 and is covered by a tear tab (not shown) similar to 22 of FIG. 2.

FIG. 4 also shows a second needle 40 in a protected position. The needle can be used separately to administer the contents of a portion of compartment 29. In this embodiment, the compartment is segmented and sealed and divided by a seal extending along line 41. It is clear that each of the four sides of the compartment may be adapted similarly to house a needle in a protected position and to administer fluid from a dedicated portion of the compartment associated with each needle.

Figure 5:
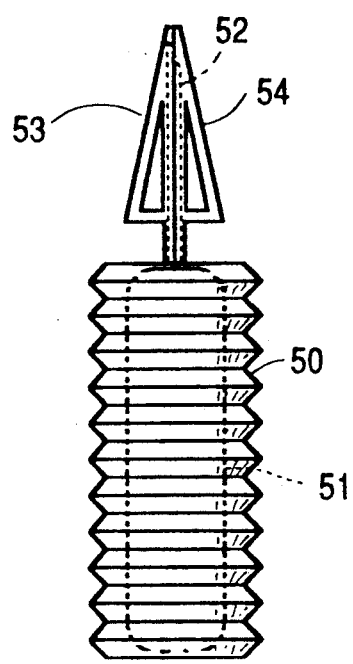
Figure 6:
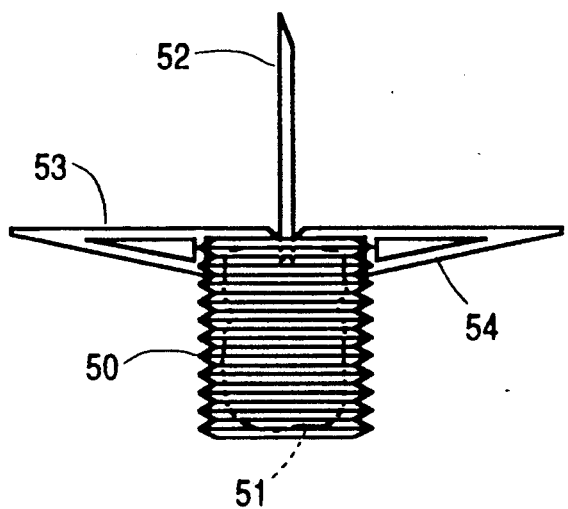

FIGS. 5 and 6 show an embodiment in accordance with the principles of this invention using an accordion squeeze bag 50 which contains a soft inner bag 51. The inner bag contains the fluid. The needle is contained within a housing defined by hinged portions 53 and 54. The hinged portions are separated to form a finger grip and to expose needle 52 as shown in FIG. 6. When accordion bag 50 is squeezed to administer the contents of bag 51, bag 51 is collapsed and remains in the collapsed position. For safe disposal, hinged portions 53 and 54 are snapped together. The inner bag, once collapsed, cannot be refilled.

Figure 7:
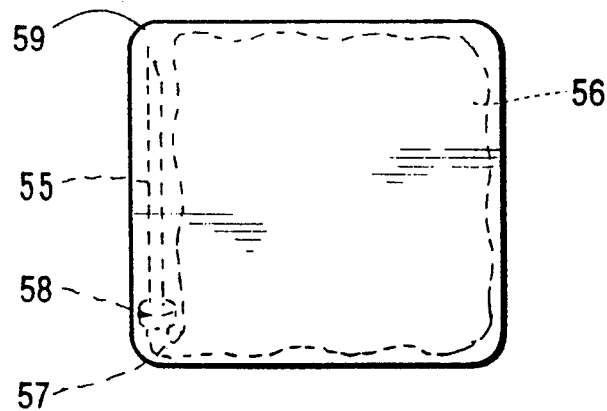
Figure 8:
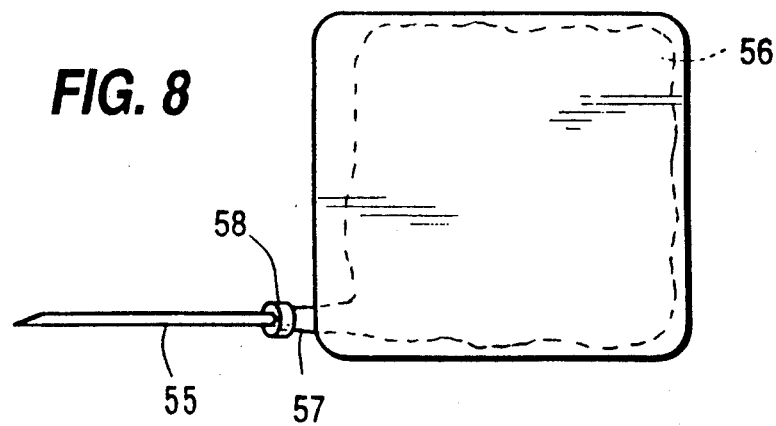

FIGS. 7 and 8 show an embodiment wherein a needle 55 is connected to a plastic squeeze bag 56 by an unstructured flexible plastic fitting at 57 in the manner of a bagpipe where the needle is analogous to the pipe of the bagpipe. The plastic is shrink-fitted onto an end of needle 55. The needle conveniently has an enlarged shoulder 58 to ensure that leakage of the contents of the bag does not occur.

FIG. 7 shows needle 55 in the protected position inside a pocket 59. Pocket 59 includes a tear strip, not shown, which is removed to allow needle 55 to assume the position shown in FIG. 8.

Figure 9:
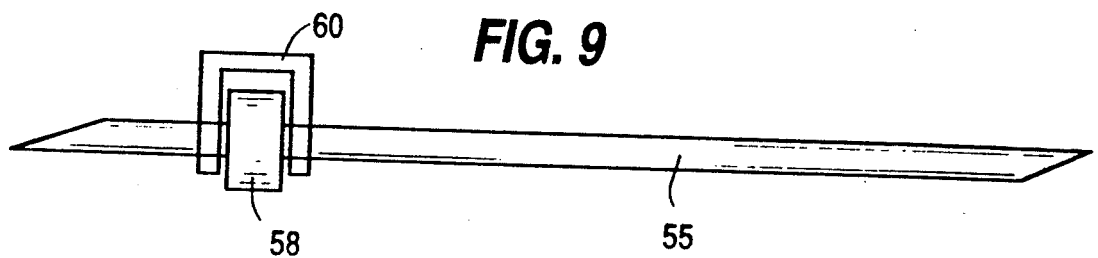
FIG. 9 shows a chuck for positioning a needle of FIG. 8 for fluid administration.

It is noted that neither the needle nor the bag in FIG. 8 is structured to administer the contents of bag 56. In use, the embodiment of FIGS. 7 and 8 is adapted to reside in a chuck which grips the needle. Once the needle is secured in the chuck, the contents of the bag are easily administered. FIG. 9 shows such a chuck 60. Chuck 60 engages enlarged shoulder 58 of needle 55 for insertion into a patient.

The embodiment of FIGS. 7 and 8 is easily employed for mass inoculation procedures where large numbers of squeeze bags of the bagpipe structure are produced in a bandoleer by form and fill equipment.

The embodiment of FIGS. 1 through 4 are also adapted for production by conventional form and fill techniques. In accordance with such techniques, two thin plastic layers are supplied from two spaced apart spools into juxtaposition where the layers are sealed at the bottom and on the sides. The resulting pocket is filled with fluid and sealed. The pockets, now filed, constitute the compartment of the embodiment of FIGS. 1-4 and 7 and 8 and a succession of such filled pockets (viz: baggies) are automatically joined together to form a bandoleer.

Figure 2:
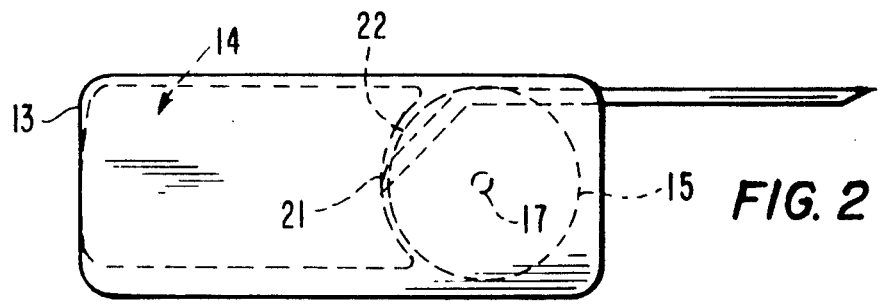
Figure 10:
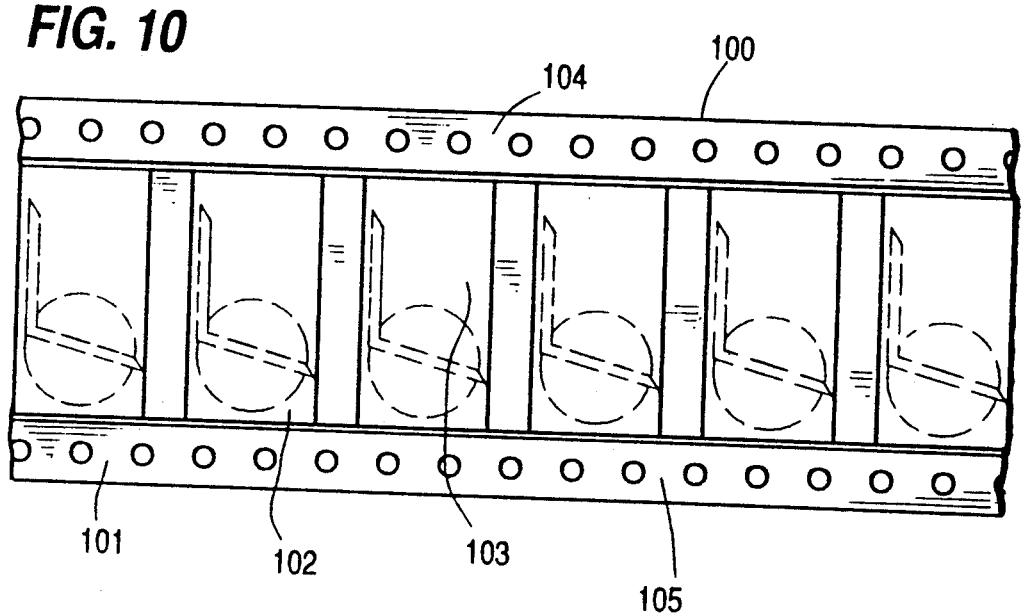
FIG. 10 shows a portion of a bandoleer of containers and needles for mass inoculation uses.

FIG. 10 shows one example of a bandoleer of fluid containers of the type shown in FIG. 1. The containers are of the credit card shape as shown in FIGS. 1 and 2, and are joined as shown to create a continuous strip of containers.

The bandoleer of filled containers (viz: tiny baggies) is now in condition for use with attached needles.

A bandoleer of baggies can be housed in a cartridge or merely supplied in strips adapted for use in a gun. Embodiments of this type are useful for rapid "shot", mass inoculations or for use in animal injections.

The bandoleer is inserted into the gun so that the needle (for example) is rotated for communication with the fluid compartment in response to the release of the gun trigger and moved to a position for fluid administration. When the trigger of the gun is squeezed, the contents of a baggie are discharged through a needle, the needle is rotated to return to the protected position and the exhaust baggie and needle are ejected for later disposal and/or destruction. Once used, the needles and baggies cannot be refilled for reuse. A next baggie and needle are connected by a plastic strip and moved to a position for inoculation when the trigger is next squeezed. The discharge of the contents of a baggie is accomplished, for example, by a roller (not shown) which is moved to squeeze out the baggie as a finger squeezes the trigger.

In each embodiment, a needle and a baggie are attached for fluid administration with no possibility of removing the needle without destroying the container thus precluding further use. Also, in each embodiment, the needle can be moved to a protected position, while still attached to the baggie, for safe disposal and a tear strip covers the needle in the protected position prior to use.

For bandoleer-type embodiments, no tear strip is necessary because the compartments are sealed to one another and are not opened until the trigger is squeezed and one compartment is detached from the bandoleer.

FIG. 10 shows a bandoleer 100 for use in a gun for i.e. mass inoculation purposes. The bandoleer includes a sequence of (credit card-shaped) squeeze bags 101, 102, 103 - - - attached to one another into a strip as shown. The strip includes side portions 104 and 105 (plastic strips) which includes holes for engaging sprockets much in the manner of movie fluid advancement in a camera or projector.

Figure 11:
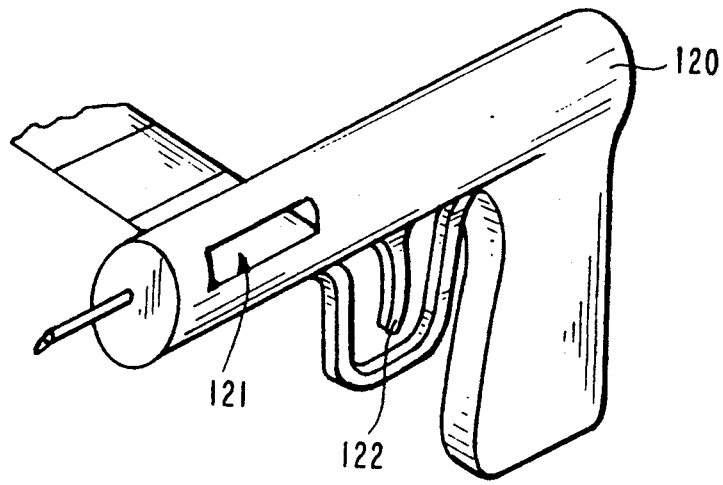
FIG. 11 shows a gun for use with the bandoleer of FIG. 10.

FIG. 11 shows in a gun 120 for use with the bandoleer of FIG. 10. The bandoleer is fed into the aperture 121, a syringe at a time, in response to the release of trigger 122. The release of the trigger also rotates the disc of the syringe and expels the previous syringe. The next time the trigger is released, the contents of the newly positioned syringe is expelled.

Any mechanical arrangement to achieve the requisite motion is suitable. A conventional double sprocket arrangement for moving the bandoleer and for rotating a disc is suitable and well understood in the art. The ejection of the expelled syringe also is well understood as are the mechanisms for squeezing the squeeze bag. Those mechanisms are not discussed in detail here.

What is claimed is:

1. A syringe for administering fluids, said syringe comprising a sealed, hand-squeezable receptacle including the fluid to be administered and a needle permanently attached to the outside of said receptacle, said syringe also including a compartment for maintaining said needle in a protected position, said syringe including means for rotating said needle, said means for rotating being of a geometry to permit movement of said needle controllably between said protected position and an exposed position for administering said fluid independently.

2. A syringe as set forth in claim wherein said means for moving includes means for returning said needle to said protected position for safe disposal.

3. A syringe as set forth in claim 2 wherein said compartment has a plurality of edges at least one of which is adapted for maintaining said needle in protected positions, and said means for moving comprises a hinge and plunger arrangement operative for moving the plunger to perforate said compartment when said needle is moved to an exposed position and to withdraw said plunger when said needle is moved to said protected position.

4. A syringe as set forth in claim 3 wherein a plurality of said edges is adapted for maintaining needles in a protected position and said means for moving comprises a plurality of hinge and plunger arrangements for moving a plunger when an associated needle is moved between the concealed and exposed position for that needle.

5. A syringe as set forth in claim 4 also including a plurality of tear tabs each sealing an associated compartment when a needle is in its protected position therein.

6. A syringe as set forth in claim 2 wherein said compartment includes a flexible outlet and said needle is attached to said outlet in the manner of the pipe of a bagpipe.

7. A plurality of syringes as set forth in claim 6 connected in a bandoleer.

8. A chuck for the rigid positioning of a needle of a syringe as set forth in claim 7.

9. A syringe as set forth in claim 6 in combination with a chuck for positioning said needle for the administration of the contents of said syringe.

10. A syringe for administering fluids, said syringe comprising a sealed squeezable receptacle including the fluid to be administered and a permanently attached needle, said syringe also including a compartment for maintaining said needle in a protected position, said syringe also including means for moving said needle controllably from said protected position to an exposed position for administering said fluid, wherein said needle is bent into first and second portions and said means for moving includes a movable disc, said second portion being mounted on said disc and operative to extend said first portion to said exposed position when said disc is rotated in a first direction and to withdrawn said first portion when said disc is rotated in a second direction.

11. A syringe as set forth in claim 10 wherein said receptacle is in the shape of a credit card, said compartment including a tear strip for covering said needle in said protected position.

12. A plurality of syringes as set forth in claim 10 joined together to form a bandoleer, each of said syringes including a squeezable receptacle and a permanently attached needle which occupies either a protected or an exposed position controllably, said syringes being connected in a strip.

13. A bandoleer as set forth in claim 12 wherein each of said syringes includes a needle which is bent into first and second positions and a disc, said second portion being attached to said disc, said needle being moveable between protected and exposed positions by rotation of said disc in first and second directions.

14. A bandoleer as set forth in claim 12 wherein each of said syringes includes a hinge for connecting a needle to said fluid compartment, said needle being rotatable from a protected to an exposed position in a manner to perforate said compartment to provide a path for fluid through said needle.

15. A gun for rapid "shot" administration, said gun being operative on a bandoleer as set forth in claim 12, said gun including means for advancing a syringe in said bandoleer to a position for fluid administration, means for moving the needle of said syringe from a protected to an exposed position, and means for expelling the fluid in said syringe.

* * * * *